(12) United States Patent
Dao et al.

(10) Patent No.: US 7,661,541 B2
(45) Date of Patent: Feb. 16, 2010

(54) POROUS SPUN POLYMERIC STRUCTURES AND METHOD OF MAKING SAME

(75) Inventors: Kinh-Luan (Lenny) D. Dao, Randolp, MA (US); Yem Chin, Burlington, MA (US); Sheng-ping (Samuel) Zhong, Northborough, MA (US); Kshitij Mohan, Potomac, MD (US); Liem Vu, Needham, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 367 days.

(21) Appl. No.: 11/496,187

(22) Filed: Jul. 31, 2006

(65) Prior Publication Data
US 2006/0261005 A1 Nov. 23, 2006

Related U.S. Application Data

(62) Division of application No. 10/331,213, filed on Dec. 30, 2002, now Pat. No. 7,083,697.

(51) Int. Cl.
*B01D 71/06* (2006.01)
*B01D 61/14* (2006.01)
*D04H 3/02* (2006.01)

(52) U.S. Cl. .................. 210/500.22; 210/500.27; 156/167; 156/181; 427/206

(58) Field of Classification Search .......... 156/167, 156/181, 578, 296, 244.11, 356, 350, 62.4; 118/200, 202; 427/206; 428/196; 264/239, 264/241
See application file for complete search history.

(56) References Cited

U.S. PATENT DOCUMENTS

| 3,836,416 | A | 9/1974 | Ropiequet | 161/2 |
| 4,044,404 | A | 8/1977 | Martin et al. | 623/1.54 |
| 4,475,972 | A | 10/1984 | Wong | 156/167 |
| 4,925,572 | A | 5/1990 | Pall | 210/767 |
| 5,121,329 | A | 6/1992 | Crump | 364/468 |

(Continued)

FOREIGN PATENT DOCUMENTS

EP 0155003 B1 7/1990

(Continued)

OTHER PUBLICATIONS

R. Thomson et al., "Polymer Scaffold Processing," *Principles of Tissue Engineering*, R. Lanza et al., eds., R.G. Landes Co., 1997.

(Continued)

*Primary Examiner*—Krishnan S Menon
(74) *Attorney, Agent, or Firm*—Mayer & Williams P.C.; David B. Bonham

(57) ABSTRACT

A non-woven polymeric matrix for separating leukocytes from a blood sample includes a non-woven three dimensional matrix formed from polymeric fibers having a predetermined pore volume fraction including a defined channel configuration, a predetermined pore size in the range of from about 10 µm to about 250 µm, and a plurality of connections between the plurality of fibers. The matrix is configured so as to remove at least about 98% of leukocytes from at least one unit of packed red blood cells. Methods of making and using the matrix are also provided.

22 Claims, 4 Drawing Sheets

U.S. PATENT DOCUMENTS

| | | | | |
|---|---|---|---|---|
| 5,340,433 | A | 8/1994 | Crump | 156/578 |
| 5,402,351 | A | 3/1995 | Batchelder et al. | 364/468 |
| 5,665,233 | A | 9/1997 | Fukuda et al. | 210/483 |
| 5,800,721 | A * | 9/1998 | McBride | 210/806 |
| 5,820,755 | A | 10/1998 | Kraus et al. | 210/483 |
| 5,936,861 | A | 8/1999 | Jang et al. | 364/468.04 |
| 6,056,993 | A | 5/2000 | Leidner et al. | 427/2.25 |
| 6,146,567 | A | 11/2000 | Sachs et al. | 264/113 |
| 6,176,874 | B1 | 1/2001 | Vacanti et al. | 623/1.44 |
| 2002/0113331 | A1 | 8/2002 | Zhang et al. | 264/40.1 |

FOREIGN PATENT DOCUMENTS

| | | |
|---|---|---|
| EP | 0406485 A1 | 1/1991 |
| FR | 2821762 A | 9/2002 |
| JP | 3-173824 | 7/1991 |
| WO | WO 01/87575 A2 | 11/2001 |

OTHER PUBLICATIONS

A. Mikos et al., "Preparation of poly(glycolic acid) bonded fiber structures for cell attachment and transplantation," *J. Biomed. Mater. Res.*, vol. 27 (1993): 183-189.

Leidner et al., "A novel process for the manufacturing of porous grafts: Process description and product evaluation," *Journal of Biomedical Materials Research*, vol. 17 (1983): 229-247.

Wnek et al., "Electrospinning of Nanofiber Fibrinogen Structures," *Nano Letters*, vol. 3 (2003): 213-216.

Kaihara et al., "Silicon Micromachining to Tissue Engineer Branched Vascular Channels for Liver Fabrication," *Tissue Engineering*, vol. 6 (2000): 105-117.

Hutmacher, Dietmar W., "Scaffolds in tissue engineering bone and cartilage," *Biomaterials*, vol. 21(2000): 2529-2543.

Zien Iwan et al., "Fused deposition modeling of novel scaffold architectures for tissue engineering applications," Biomaterials, vol. 23 (2002): 1169-1185.

Shinichiro, Kuroda, "Patent Abstracts of Japan," vol. 0154, No. 21 (C-0878). Oct. 25, 1991, JP 3-173824A.

* cited by examiner

POROUS SPUN POLYMERIC STRUCTURES AND METHOD OF MAKING SAME

STATEMENT OF RELATED APPLICATION

This patent application is a divisional of U.S. patent application Ser. No. 10/331,213, filed Dec. 30, 2002, entitled "Porous Spun Polymeric Structures and Method of Making Same," now U.S. Pat. No. 7,083,697, which is incorporated herein by reference in its entirety.

FIELD OF THE INVENTION

The present invention relates to continuous filament nonwoven polymers made from biocompatible polymers. More particularly, the present invention relates to porous three-dimensional non-woven polymer matrices useful in removing leukocytes from blood suspensions as well as methods of making same.

BACKGROUND OF THE INVENTION

There are many situations in which the administration of a whole blood suspension or a component thereof is therapeutic. The nature of the condition dictates which suspension is appropriate. For example, transfusions of red blood cells are useful in patients suffering from chronic anemia which can result from disorders such as kidney failure, malignancies, or gastrointestinal bleeding. In addition, red blood cells are useful in treating acute blood loss resulting from trauma or surgery. Platelets, which are part of the blood clotting system, are useful in treating thrombocytopenia, a condition in which there is a shortage of platelets. Platelets have also been found to be helpful in treating cancer patients. Finally, although plasma is not typically used in transfusions, it is fractionated into specific products including albumin, clotting factor concentrates, and intravenous immune globulin. These fractions can be administered to a patient in need thereof.

Whole blood is typically subjected to centrifugation to separate out the three main components: red blood cells, plasma, and platelets. However, centrifugation does not provide complete separation. For example, a red blood cell suspension that has been centrifuged from whole blood will typically contain a portion of the leukocytes, some platelets, fibrinogen, fibrin strands, small fat globules, as well as small amounts of other blood components.

Regardless of the particular fraction or component of whole blood that is used, there is general agreement that the presence of white blood cells in the component is undesirable. It is believed that transfusion of blood components in which white blood cells are present has been responsible for adverse reactions ranging from a mild reaction, such as fever, to death from Graft-Versus-Host disease, in which the transfused leukocytes cause irreversible damage to the recipient's organs including the skin, gastrointestinal tract and neurological system. Thus, efficient removal of white blood cells from whole blood and blood components is needed.

To address this need, a number of materials and methods have been developed to remove white blood cells from a blood component. However, removal is not a straightforward matter of simple filtration. There are a variety of white blood cells or leukocytes including granulocytes, macrocytes, and lymphocytes. While the granulocytes and macrocytes are similar in size ($\geq 15$ microns in diameter), the lymphocytes are considerably smaller (between about 5-7 microns in diameter) and are also comparable in size to red blood cells (about 7 microns in diameter). This disparity in cell size makes simple filtration of leukocytes difficult.

In addition, a red blood cell suspension is typically contaminated with other components such as microaggregates and platelets. Microaggregates, which are small aggregates of components such as red blood cells, leukocytes and platelets, occur in blood that has been stored for extended periods of time, and can be up to 200 microns in diameter. Platelets, although smaller in size than micro aggregates, tend to be adhesive. The microaggregates and platelets can collect on or within pores of a simple filter and can cause clogging thereof. Due to the above, there is a present need for a product that is able to efficiently remove leukocytes without becoming clogged with microaggregates and the like.

Typically, when blood is drawn from a donor, approximately 450 ml of whole blood is supplied into a bag which usually contains an anticoagulant to prevent the blood from clotting. Hereinafter, this quantity of a whole blood sample will be referred to as a unit or a unit of whole blood. As detailed above, whole blood is rarely used in ibis form. Rather, most units are processed by centrifugation, gravity settling, or otherwise, to produce a unit of red cell concentrate in blood plasma known as packed red cells (PRC).

The volume of a unit of PRC varies considerably dependent on the hematocrit (percent by volume of red cells) of the drawn blood which usually falls within the range of from 37% to 54%. The hematocrit of the PRC usually falls within the range of from 70% to 80%. As a result, most units of PRC fall within the range of from 250 to 300 ml. However, variations below and above these figures are not uncommon.

For the purposes of convenience, as well as to more safely maintain the sterility of the blood sample, it is desirable for a leukocyte removal device to efficiently remove the leukocytes from a unit of whole blood or a unit of PRC. Thus, it is desirable for leukocyte removal device to efficiently remove leukocytes from about 500 ml of whole blood or 250-300 ml of PRC. Furthermore, in order to minimize the detrimental effects of the leukocytes, efficient removal in excess of 98% of each of the different types of leukocytes is desirable.

Leukocyte Separation

U.S. Pat. No. 4,925,572 to Pall discloses filtration devices using fibrous, non-woven media to capture leukocytes from a blood suspension. The device includes a series of porous elements having successively smaller pore diameters. The porous elements include synthetic resins such as polyvinylidene fluoride, polyethylene, polypropylene, cellulose acetate, nylon 6 and 66, polyester, polyacrylonitrile and polyaramid. These polymers are formed into fibers using a melt blowing process. However, the polymeric filtering media formed in this fashion have a surface tension which resists flow of liquid into the filtering media. The media may then require modification by surface grafting monomers onto the formed polymer in order to improve the wetting characteristic.

U.S. Pat. No. 5,820,755 to Kraus et al. discloses a filter unit and method of removing leukocytes which includes a commercially available nitrocellulose membrane having a pore size of 5-15 microns. The filter unit includes a plurality of layers, at least two of which are non-woven fibrous material as prefilter elements and one or more which is the nitrocellulose membrane. The filters may optionally be chemically modified by performing a surface grafting reaction with a monomer. Flow rates determined for various configurations of membrane diameters and pore sizes and ranged from 0.5 ml/min using fresh and aged blood samples. The flow rates were in the range of about 0.5 ml/min to 50 ml/min and diminished as prefilters were added to remove larger particles in the aged blood. It appears that the flow rate and ability to filter larger amounts of blood are reduced when this method is used on aged blood. Another disadvantage of this invention is the complexity of design which requires at least three separate elements to perform the separation function.

European Patent Application 155,003 to Asahi discloses a packed column having a main filter of fibers having an average diameter of from 0.3 microns to less than 3 microns, a bulk density of from 0.01 $g/cm^3$ to 0.7 $g/cm^3$, and an average distance between two adjacent filters defined by an equation whereby the average distance is in the range of from 0.5 microns to 7.0 microns. The fibers are selected from a variety of synthetic fibers such as polyesters, polypropylenes, and the like, to natural fibers. The fibers are made by blowing air or high-pressured steam on a mass of fibers and bonding them to one another. Alternatively, the fibers may be entangled and bonded with either heat or an adhesive. The fibers are oriented perpendicular to the direction of blood flow. A prefilter may optionally be used on blood having microaggregates.

European Patent Application 0 406 485 A1 discloses a filter unit and a method of removing leukocytes which includes a non-fibrous continuous pore matrix foam or membrane as the filter. The matrix has a distribution of pore sizes along a gradient. On the upstream side the element has larger pores and on the downstream side the element has smaller pores. As in the aforementioned filter units, this filter also has a randomized pattern of fiber distribution and pores, albeit with a non-randomized porosity gradient from large to small in the direction of flow of the suspension.

A disadvantage of each of the aforementioned filters is that they possess a randomized pattern of fiber distribution or foam porosity which includes a randomized pattern of pore channels. This arrangement can have the effect of reducing the flow rate of blood through the filter without having an associated improvement in removal efficiency. Furthermore, this configuration is more likely to cause clogging of the filter with a reduced capacity with respect to the total amount of blood that may be separated using the filter.

Methods of Making Porous Polymeric Materials

Conventional methods are known for use in making a variety of biocompatible polymeric materials such as the aforementioned leukocyte blood filtering materials. In addition to the methods listed above, the conventional methods also include solvent casting, particulate leaching, melt molding, phase separation, in situ polymerization, and membrane lamination. Thomson, R. et al., "Polymer Scaffold Processing," *Principles of Tissue Engineering*, Lanza R. et al., eds., R.G. Landes Co. (1997).

In solvent casting, salt particles are dispersed in a polymer solution, for example a poly(L-lactic acid)/chloroform solution and cast into a container. The salt is insoluble in the solvent and forms crystal structures in the solution. The solvent is evaporated and the salt is removed from the resultant polymer layer by immersion in water or a heat treatment. The pores are the spaces that were filled by the salt. Membranes formed in this manner may attain porosity of up to about 93% and possess inter-connected pore channels. These membranes, however, are two dimensional and must be laminated, for example by application of additional chloroform, in order to form a three dimensional structure.

Foams and sponges are commonly formed from synthetic or natural polymeric materials using phase separation. In particular, phase separation upon freeze-drying has been used extensively. The polymeric materials are dissolved in a suitable solvent and rapidly frozen. The solution is then freeze-dried which removes the solvent and leaves behind a porous structure. Materials fabricated from natural polymers using this technique typically have average pore sizes ranging from 1-250 microns, depending on freezing conditions. However, in most applications where foams or sponges are helpful, the average pore size is preferably about 50-150 microns.

It is also known to form porous matrices by using the technique of fiber bonding. One such method uses poly(L-lactic acid) ("PLLA") dissolved in methylene chloride to Loin a liquid which is cast over a non-woven mesh of poly (glycolic acid) (PGA) fibers. Methylene chloride is not a solvent for PGA. The solvent is then removed and the PLLA/PGA composite is heated to a temperature above the melting point of PGA. This allows the PGA to form bonds where the fibers overlap one another. The PLLA is then selectively dissolved in methylene chloride to remove it from the matrix. Mikos A. et al., "Preparation of poly(glycolic acid) bonded fiber structures for cell attachment and transplantation," *J. Biomed. Mater. Res.*, 27:183-89 (1993). In addition to being complex, this method has the disadvantage of using, in this case, a solvent known to be carcinogenic. Residual solvent left in the matrix could therefore pose a health hazard if it is subsequently released from the matrix into the treated blood sample. In addition, this technique does not lend itself to easy and independent control of porosity and pore size.

U.S. Pat. No. 4,475,972 to Wong discloses a porous polymeric material suitable for use as a vascular graft as well as a method of making same. The method involves extruding a viscous solution of a biocompatible polymer from a spinneret to form a plurality of filaments wound on a rotating mandrel. The contact of the wet filaments are points where the filaments become bound to one another after the solvent is evaporated. A thickness of 500 microns is achieved by approximately 800 passes of the spinneret over the mandrel. The pore size can be adjusted by varying the size of the fibers as well as the angle of the spinneret with respect to the mandrel known as the winding angle.

U.S. Pat. No. 6,056,993 to Leidner et al. discloses a porous tubular synthetic prosthesis and a method of making same. The method involves electrostatic spraying of both a water-soluble and a water-insoluble fibrous component onto a rotating mandrel or mold to form a prosthesis precursor. Next, to create porosity in the prosthesis, the water-soluble fibrous component is at least partially removed. The water-soluble fiber portion acts as a spacer, the removal of which creates porosity in the prosthesis. However, the method does not permit selection of the size, shape, location, or design of the pores forming the internal architecture of the prosthesis, because the electrostatic spray system involves a random application of fibers.

Each of the conventional methods form a material having characteristics and limitations which preclude use of the formed material in more than a few medical applications. Furthermore, the materials formed from conventional methods are often not optimal even for the few applications for which they have been designed. As a result, there is a present need for a material having structural and other parameters which make it suitable for a variety of medical applications. There is also a need for a method of making such a material.

SUMMARY OF THE INVENTION

The present invention relates to a porous non-woven matrix being sufficiently variable in the parameters of tensile strength, porosity, and shape, so as to be compatible with a variety of medical applications in which biocompatible polymeric matrixes may be used. In particular, the present invention relates to a porous non-woven matrix useful in leukocyte separation applications. The present invention further relates to an apparatus and a method of making a porous non-woven matrix.

In one aspect of the present invention, an apparatus for making a three dimensional non-woven matrix made from a polymer is provided including a moveable table capable of motion in a first plane (x) and a second plane (y) perpendicular to the first plane, a control member for controlling the movement of at least the table, and an applicator for applying at least one liquid polymeric fiber to the table.

In a further aspect of the invention, a method of making a three-dimensional non-woven porous polymeric matrix is provided including the steps of providing at least one liquid polymer capable of forming a fiber; feeding the polymer through at least one applicator to form at least one polymeric fiber; applying the polymeric fiber in a plurality of layers onto a moveable table which is capable of motion in at least a first plane (x) and a second plane (y); and controlling at least a motion of the table so as to form a three-dimensional non-woven porous polymeric matrix comprised of interconnected fibers.

In another aspect of the invention, a method of making a three-dimensional non-woven matrix is provided including the steps of admixing at least one fiber-forming polymer with a compatible solvent to form a flow able polymer mixture; applying at least one fiber formed from the polymer mixture to a moveable table capable of motion in a first plane (x), a second plane (y) perpendicular to the first plane and a third plane (z) perpendicular to the x and y planes; and controlling movement of at least the table so as to form a three dimensional non-woven matrix of fibers having a predetermined pore volume fraction including a defined channel configuration, a predetermined pore size, and a plurality of connections between the plurality of fibers.

In a still further aspect of the present invention, a non-woven matrix material for use in a medical device is provided, with the matrix material being made according to one of the aforementioned methods.

In another aspect of the present invention, a non-woven porous polymeric matrix for separating leukocytes from a blood sample is provided including a non-woven three dimensional matrix formed from polymeric fibers having a diameter of from about 5 µm to about 15 µm, the matrix having a predetermined pore volume fraction including a defined channel configuration, a predetermined pore size in the range of from about 10 µm to about 250 µm, and a plurality of connections between the plurality of fibers. The matrix is configured so as to remove at least about 98% of said leukocytes from at least one unit of packed red blood cells.

In an additional aspect of the invention, a separation unit is provided for separating leukocytes from a sample including a supply member for supplying a blood sample from which leukocytes are to be separated; a housing in fluid communication with the supply member, the housing including an inlet and an outlet and defining a fluid flow path therebetween; a matrix material according to the invention arranged in the housing for separating the leukocytes from the blood sample, wherein the matrix material has a first upstream side and a second downstream side, the first side being arranged toward the inlet and the second side being arranged toward the outlet; and a collection member in fluid communication with the housing for collecting the blood sample from which leukocytes have been separated.

In another aspect of the invention, a method of separating leukocytes from a blood sample includes passing a blood sample containing leukocytes through a separation unit of the present invention.

DETAILED DESCRIPTION OF THE PREFERRED EMBODIMENTS

Methods of Making Porous Polymeric Materials

Figure 1:
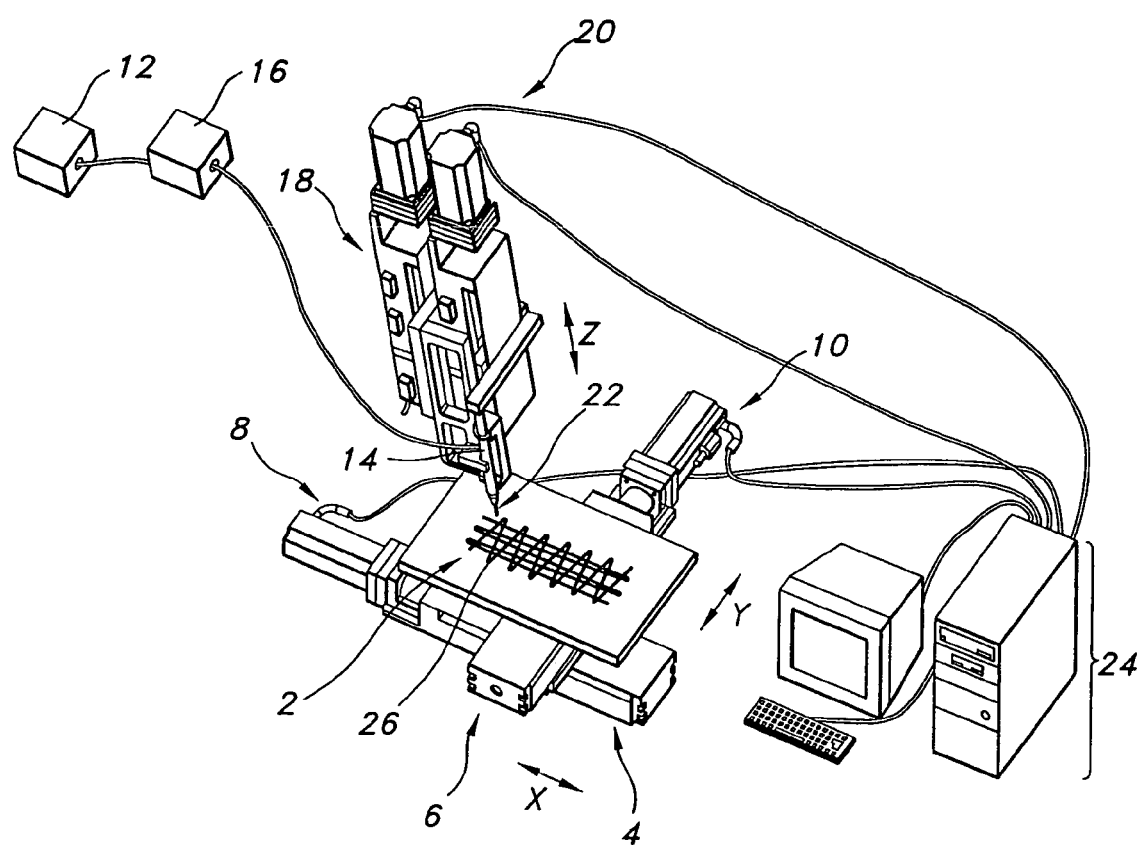
FIG. 1 is a schematic view of an apparatus for making a three dimensional non-woven polymeric matrix according to the present invention.

The non-woven porous polymeric material of the present invention is made by extruding a natural, synthetic or combination biocompatible polymer dissolved in a suitable miscible solvent or melted to form a viscous solution from which a continuous fiber may be drawn. The solution is extruded under pressure and fed at a certain rate through an applicator having an opening or openings of a predetermined size to form a fiber or fibers. A desired fiber diameter, typically from about 1 to about 40 microns, preferably from about 5 to about 15 microns, is formed into a desired material by the actions of a moveable horizontal machining center referred to herein as a moveable table, an application table or simply as the table. The movement of the table is controlled so as to apply the fiber or fibers in any desired configuration.

In one desirable aspect of the invention, movement of the table is controlled by using motion-controlled drives which may be programmed by computer software. There are individual drives for each of the three directions. The drives may be programmed for speed, acceleration and position using a motion controller. The system is accurate to within 0.001" tolerances in all directions. Thus, the rate of deposition, elongation, and stretch of the fiber is precisely regulated byte programmed motion of the table, and optionally the applicator, in relation to the table.

There are no particular limitations to the type of material that may be used to form the leukocyte filter so long as it is capable of being formed into fibers having sufficient strength to tolerate the stress involved in applying the fibers onto the moveable table. Natural polymers, synthetic polymers, or combinations thereof may be used. It is possible, for example, to use a mixture of a non-fiber forming polymer and a fiber forming polymer, wherein the non-fiber forming polymer is present in a small enough percentage of the total mixture to impart desired properties, while still allowing formation of a fiber for application onto the moveable table.

The polymers may be biodegradable, biostable, or a combination thereof. Biodegradable synthetic polymers are preferred and include poly a-hydroxy acids such as PLLA, PGA and copolymers thereof (i.e., poly D,L-lactic co-glycolic avid (PLGA)), and hyaluronic acid. Poly α-hydroxy acids are approved by the FDA for human clinical use.

Examples of some biodegradable natural polymers useful in the invention include polysaccharides such as alginate, cellulose, dextran, polyhyaluronic acid, chitin, poly(3-hydroxyalkanoate), poly(3-hydroxyoctanoate) and poly(3-hydroxyfatty acid). Also contemplated within the invention are chemical derivatives of said natural polymers including substitutions and/or additions of chemical groups such as alkyl, alkylene, hydroxylations, oxidations, as well as other modifications familiar to those skilled in the art.

Further examples of suitable biodegradable elastomers are described in U.S. Pat. Nos. 4,045,418, 4,057,537 and 5,468,253, which are hereby incorporated by reference in their entireties. In addition, non-limiting examples of some useful composites of natural and synthetic polymeric materials for scaffolding applications are disclosed in Chen, G., et al., *Advanced Materials,* 12:455-457 (2000), which is hereby incorporated by reference.

As used herein, "biodegradable" materials are those which are broken down and/or absorbed by the body. Examples include materials containing bonds that may be cleaved under physiological conditions, including enzymatic or hydrolytic scission of the chemical bonds.

Bio-stable polymers are also useful in the invention, and include, for example, olefin polymers including polyethylene, polypropylene, polyvinyl chloride, polytetrafluoroethylene, polyvinyl acetate, polystyrene, poly(ethylene terephthalate), polyurethane, polyurea, silicone rubbers, polyamides, polycarbonates, polyaldehydes, natural rubbers, polyetherester copolymers, styrene-butadiene copolymers, and combinations thereof.

Advantageously, polyurethanes are used alone or in combination with other polymers to make the device of the invention. Polyurethanes can be tailored to possess varying characteristics of flexibility and degradability by varying the degree to which they contain cleavable sites. The polyurethanes generally possess, or can be modified to possess, desirable mechanical characteristics of tensile strength and modulus of elasticity, which are useful in withstanding stress of fluid flow through the leukocyte filter, particularly when the fluid passes through the filter under pressurized conditions.

Polyether polyurethanes exhibit more bio-stability than polyester polyurethanes, although both find use in the present invention. The polyurethanes can range from those that are substantially free of ether and ester linkages, such as segmented aliphatic polyurethanes of U.S. Pat. No. 4,873,308, which is incorporated by reference herein, to those having such ether and ester linkages. Commercially available segmented polyurethanes include Biomer™ (Ethicon, Inc., Somerville, N.J.), Pellethane™ (Dow Chemical, Midland, Mich.), and Tecoflex™ (Thermedics, Inc. Woburn, Mass.). Typically, polyether polyurethanes exhibit more bio-stability than polyester polyurethanes. The degree of bio-stability, as well as the mechanical characteristics, can be modified by varying the amount and type of cleavable linkages using techniques and design strategies that are well known in the art.

Further examples of synthetic polymers useful in the invention include polyphosphazenes, poly(vinyl alcohols), polyamides, polyester amides, poly(amino acids), polyanhydrides, polycarbonates, polyacrylates, polyalkylenes, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglyxolides, polysiloxanes, polycaprolactones, polyhydroxybutrates, styrene isobutyl styrene block polymers, polyurethanes and copolymers and blends thereof.

The polyanhydrides and polyesters contain labile bonds and are known for their hydrolytic reactivity. It is therefore contemplated within the invention to regulate the hydrolytic degradation rates of these polymers as needed by changing the polymer backbone and sequence structure accordingly.

The matrix of the present invention can be produced from fibers formed by diluting the desired polymer in an appropriate solvent. Non-limiting examples of appropriate solvents include tetrahydrofuran, dimethyl acetyl chloride, toluene, xylene, and calcium chloride. Choice of solvent will be based on the polymer used and is well within the ken of a practitioner in the art. Desirably, the viscosity of the solution will be within the range of from about 200,000 cps to about 600,000 cps.

Optionally, a cross-linking agent may be added from a separate source to the solution just prior to application of the mixture to the table so as to assist in fiber formation. In particular, water-soluble polymers including polysaccharides such as alginate, require a crosslinker to render it water-insoluble after fiber formation. Suitable cross-linking agents for these polymers include metal ion solutions, such as the salts of calcium, copper, aluminum, magnesium, strontium, barium, tin, and zinc. Particularly desirable cross linking agents for natural polymers, particularly alginate, include calcium chloride ($CaCl_2$), strontium chloride ($SrCl_2$) and calcium gluconate (Ca—Gl). Cross linking agents suitable for use with collagen include aldehydes such as gluteraldehyde and carbodiimides. When using a cross-linker, it is important to introduce the cross-linker just prior to, or just after, formation of the fiber. For example, it is possible to have a two-chamber feed design in which the polymer solution and cross-linking agent are introduced just prior to entry into the applicator or spinneret. Alternatively, it may be possible to form a fiber from the uncrosslinked material and then pass the fiber into a bath containing the cross-linker prior to application onto the table.

It is contemplated as within the invention to use the polymers alone, as copolymers, or blends thereof. Selection of the polymer combinations will depend upon the particular application and include consideration of such factors as desired tensile strength, elasticity, elongation, modulus, toughness, viscosity of the liquid polymer, whether biodegradable or permanent structures are intended, and the likes to provide desired characteristics.

One having skill in the art may select appropriate combinations based on the desired characteristics of the matrix and what is known in the art regarding the individual polymers of interest. For example, polyanhydrides and polyvinyl chlorides are known to introduce flexibility into a polymer. It is possible, therefore, to use a small amount of certain polymers as additives to impart desired properties to the main polymer or polymer blend. For example, by adding some polyanhydride to a PLA polymer, flexibility of the structure formed thereof is increased. Small amounts of a non-biodegradable polymer may be added to a biodegradable polymer without compromising the biodegradability of the final material formed thereof. Selection of polymer blends, copolymers, and additives will be based on the particular end use of the polymeric matrix structure and can be made accordingly by one having ordinary skill in the art. It is therefore within the contemplation of the invention to employ multiple polymers, polymer blends, copolymers, and additives to maximize desirable matrix properties. In one desirable aspect of the invention, a matrix is made from a polymer including about 70% polylactic acid and about 30% polyurethane.

Furthermore, it is specifically contemplated by the inventors that matrices of the present invention may be created by alternately applying or simultaneously applying more than one polymer or copolymer. For example, it is possible to apply two different polymeric fibers by using two applicators to apply two different polymers or polymer blends simultaneously. Alternatively, it is possible to apply a first polymeric fiber in a first layer or layers, and apply a subsequent second polymeric fiber or fibers in a subsequent layer or layers. By alternating the polymer, a matrix can be made having varying properties depending on the distribution of each of the polymer, copolymer or blends within the matrix.

Varying the size of the applicator opening or openings, rate of feed of the liquid, and movement of the table, allows for a three dimensional matrix to be formed having any desired shape and size up to any desired thickness. Moreover, the pore size and pore volume fraction are similarly controlled by the rate of feed, size of applicator openings and movements of the table, and can be varied at will.

Additionally, it is possible to alter the shape of the tip of the applicator or nozzle to vary the cross-sectional shape of the fiber. For example, a circular, oval, elongate, star, or irregularly shaped nozzle can vary the cross section of the fiber drawn therethrough. This adds a further dimension of microarchitecture which can be varied to alter the flow-through characteristics of the final product. An irregularly shaped fiber may have superior flow characteristics and leukocyte removal efficiency as compared to a similarly formed leukocyte filter having a spherical cross-sectional shape.

A matrix of the present invention may be formed as a sheet having a uniform pore volume fraction and pore size throughout the sheet. Alternatively, the matrix may have a gradient of pore volume fraction and pore size through a cross-section thereof. Additionally, the matrix may be formed as a tube having a gradient beginning with a first predetermined pore volume fraction and pore size at an internal diameter of the tube which gradually changes along its cross section to a second predetermined pore volume fraction and pore size at an external diameter of the tube. It is also possible to program the movements of the applicator and table to provide a matrix having a randomized structure within any predetermined ranges of pore sizes and pore volume fraction.

Rather than have a uniform pore size, for example from a pre-set wind angle in spinning a fiber about a mandrel, the present invention allows for substantially continuous modification of the pore size as well as other parameters of the matrix.

The apparatus and method of the present invention is capable of forming a porous matrix which is similar in size, shape, and strength to that formed by the method of the prior art. However, the apparatus and method of the present invention has capabilities well beyond that of the prior art methods. Whereas the prior art method forms one particular internal architecture, which is often random and uncontrolled, the present invention is not so limited. Specifically, the method of the present invention allows for a wide variety of specific predetermined internal architectures. The method allows for specific design of pore channel configurations such as channel shape, size, and channel inter-connections. Each of these parameters may be predetermined by selecting appropriate movements of the moveable table.

Referring now to FIG. 1, a perspective view of the apparatus for making the porous matrix of the present invention is shown. The moveable table 2 is operatively attached to an x drive member 4 and a y drive member 6. Movement of the drive members 4, 6 is achieved by an x control member 8 and a y control member 10. A holding chamber 12 houses the polymer which is fed into an applicator 14 via a pump 16. The liquid polymer is fed through the applicator 14 onto the table 2. The applicator 14 may remain stationary, or may be moved in relation to the table via a z drive member 18 which is controlled by a z control member 20. Movement of the table 2 results in deposition of a fiber or fibers 22 in a layer 26 on the table 2.

The x, y, and z control members, 8, 10, and 20, are shown in operable connection to a master control 24. The master control is desirably under the control of a computer program which directs movement of the drive members 4, 6, and the applicator 14 via the control members 8, 10, and 20. Although one applicator is shown, it is possible to use two or more applicators, which are able to apply the same or different polymers or co-polymers, or blends thereof either simultaneously, sequentially or in combinations thereof. Additionally, although the z control member 20 is shown connected to the applicator 14, it is also possible for the drive member 20 to be connected to the table 2.

In operation, the table moves in a predetermined pattern so as to produce a particular predetermined fiber design. Desirably, movement of the table is directed by a master control which is programmed by a computer. A three-dimensional structure can be built up by repeating the motion of the table as many times as required to achieve the desired shape, size, and thickness of the matrix.

Figure 2A:
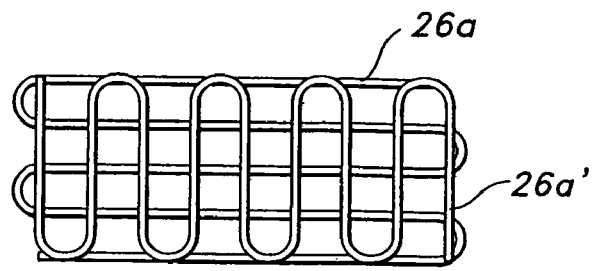
FIGS. 2A-2D are exploded top views of embodiments of internal architecture of the non-woven polymeric matrix according to the invention.

Referring now to FIGS. 2A-2D, a series of possible fiber patterns in accordance with the present invention are shown. In FIG. 2A, a first sine wave pattern is shown in a first layer 26a, and a second sine wave pattern rotated 90° from the first pattern is shown in a second layer 26a'. In one advantageous aspect, the same pattern repeats for the number of layers required to achieve the desired thickness of the matrix.

Numerous permutations of this particular pattern or design are possible. For example, the first sine wave pattern may be repeated any number of times to form a particular thickness. The second sine wave pattern may be repeated the same or a different number of times to form the same or a different thickness. Similarly, although the sine wave patterns are shown at a 90° angle in relation to one another, any relative angle may be used.

Furthermore, in FIG. 2A the sine wave is evenly spaced in a regular pattern. However, it is possible to incorporate variations in the frequency of the wave to be greater or less than the pattern shown. The variations may range from an entirely random pattern to a semi-random or non-random pattern. It is also possible to repeat the same pattern in direct alignment along the vertical or z axis on repeated passes of the applicator, or to offset vertical alignment of the fibers in relation to the previous layer or layers. In this manner, a non-woven polymeric matrix may be formed having a regular or non-regular, repeating or non-repeating internal architecture.

Figure 2B:
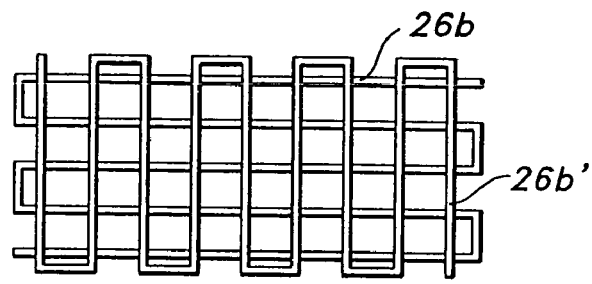
Figure 2C:
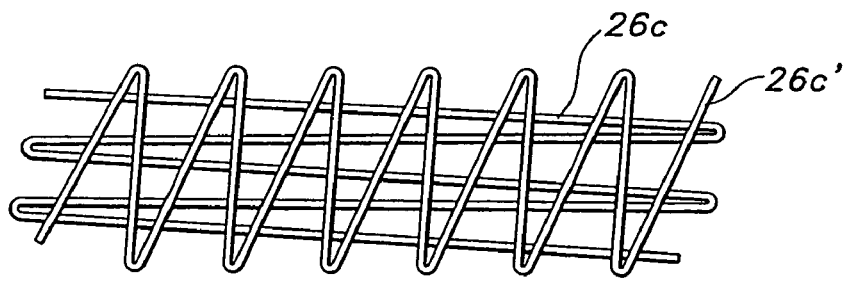

Referring now to FIG. 2B, a first and second layer 26b, 26b' of an alternative step wave pattern of fibers is shown. FIG. 2C shows a first and a second layer 26e, 26e' of a saw-toothed pattern. Here, as before, the patterns may be varied within each layer, in the angle of one layer in relation to another, and in the vertical alignment of the various layers. Furthermore, each layer may include multiple fiber patterns therein. Although a series of patterns is shown, it is to be understood that these are presented by way of example. The present invention is not limited to these patterns. Any pattern may be chosen and can be formed by directing movement of the table in relation to the fiber fed from the applicator onto the top surface of the table 2. Furthermore, multiple patterns may be combined in a single matrix and even in a single layer.

Figure 2D:
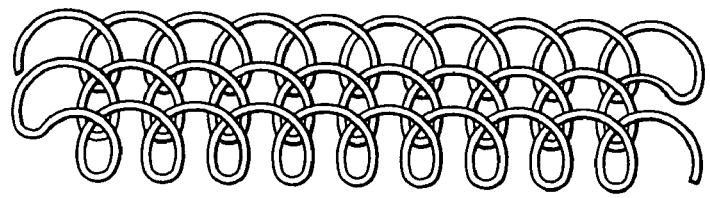
Figure 3A:
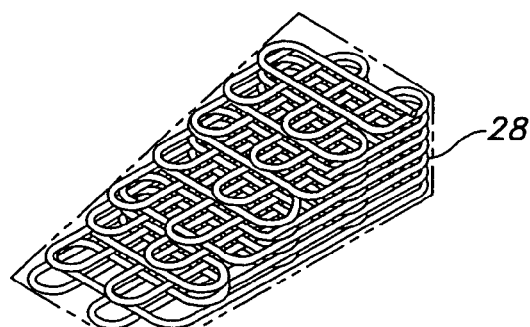
FIGS. 3A-3D are perspective views of three dimensional matrices formed according to the present invention.
Figure 3B:
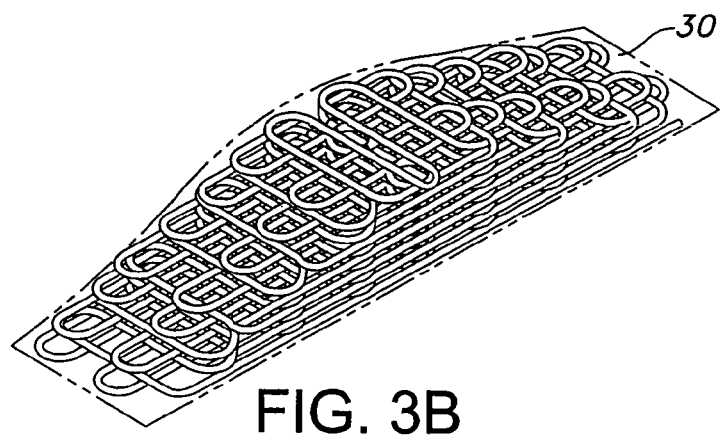
Figure 3C:
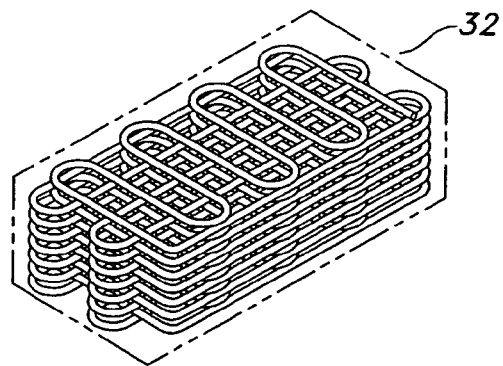
Figure 3D:
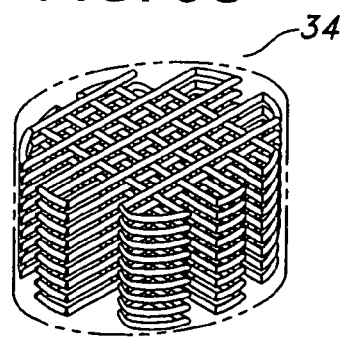

Movement of the table in the third z direction permits formation of a single layer of fiber or fibers to have a depth dimension. Referring now to FIG. 2D, a layer 26d of a concentric vertically oriented loop pattern is shown using motion of the table in the z direction (along the vertical axis) in addition to the x and y directions. In this aspect, the single layer 26d includes concentric loops arranged perpendicular to the table surface. As with the other patterns described previously, the three dimensional single layer forms may be made uniform or vary in size, they may be used alone or in combination with the two dimensional forms.

It is possible to create a first part of a matrix using one or more of the layers having a two dimensional type pattern with pores oriented vertically with respect to the surface of the table, and to periodically interrupt this first part with one or more second parts of the matrix including one or more layers of the three dimensional type pattern defining pores oriented horizontally with respect to the surface of the table. In this way, it is possible to make a matrix having a predetermined pattern of interconnected pore channels or channel configuration.

The matrices of the present invention may be made into any desired three dimensional shape. FIGS. 3A-D illustrate possible three dimensional structures of the matrix according to the invention including a wedge 28, a mound 30, a block 32, and a cylinder 34. It is to be understood, however, that the present invention is not limited to such shapes. It is possible to direct application of the fiber into any three dimensional pattern including but not limited to spheres, semi-circles, tubes, sheets, and so on. Furthermore, the matrices may have a smooth or rough surface, depending on the use thereof.

The non-woven polymeric structures according to the invention possess desirable characteristics of pore volume fraction, pore size, channel configuration, and tensile strength for a great variety of biological applications. These parameters may be varied at will to suit particular applications. Generally, the matrices of the present invention are formed from filaments having an average diameter of from about 1 µm to about 40 µm, desirably between about 5 µm to 15 µm. Any number of layers may be produced, although generally, at least 10 layers are required to maintain sufficient tensile strength of the matrix. The layers thus formed will typically be greater than about 25 µm thick. The elongation of the polymer fiber will range from about 15% to about 300% and can be controlled by the rate of feed through the applicator as well as the relative movement between the applicator and the moveable table. Pore volume fraction will be within the range of from about 15% to about 90%, depending on the application.

Tensile strength is an important parameter in polymeric matrices used in biological applications. Tensile strength is the ability of a sample to withstand a stretching force as measured by the amount of stress required to break the sample with stress being the force required to stretch (i.e., break) a sample per cross-sectional area. An Instron machine measures tensile strength, which is reported in $N/cm^2$ or $lbs/in^2$. Tensile strength of the fibers can also be varied by selection of polymeric raw materials, as discussed supra. Generally, tensile strength will be within the range of from about 0.5 $lbs/in^2$ to about 5 $lbs/in^2$ (0.35 $N/cm^2$ to 3.5 $N/cm^2$).

Another important parameter is the ability of a polymer to resist deformation, in particular indentation. Shore hardness, also known as Durometer Hardness (for the instrument used in obtaining the measurement), is measured by penetrating the sample with an indenter foot, for example using the ASTM D2240 00 test method. Results are reported in one of two scales, A or D. Desirably, the Shore Hardness of the fibers within the matrix of the present invention fall within the range of from about 50A to 70 D, and more desirably from about 70 A to about 50 D.

Leukocyte Separation

In one advantageous aspect of the invention, a leukocyte separation matrix is provided. With respect to blood filtration applications, it is important for the filter to possess sufficient tensile strength to withstand the pressure of the blood as it flows or is forced through the filter. Furthermore, by providing a stronger matrix, the present invention permits a leukocyte separation matrix according to the present invention to be relatively thinner than the filters of the prior art. This is advantageous in that a thinner filter provides less resistance to flow, permitting filtration to occur in less time, and is less prone to clogging as compared to thicker filters.

A non-woven polymeric matrix for separating leukocytes from a blood sample may be made using the method as described previously. It is possible to form a non-woven three dimensional matrix having a predetermined pore volume fraction including a defined channel configuration, a predetermined pore size, and a plurality of connections between the plurality of fibers that can remove at least about 98% of leukocytes from at least one unit of packed red blood cells. The pores may range from substantially continuous to substantially discontinuous throughout a depth of the matrix. The pores are desirably substantially parallel to one another.

The matrix for separating leukocytes possesses sufficient tensile strength to resist deformation or collapse when blood is either gravity-fed or forced through the matrix by an applied pressure. Desirably, the tensile strength of the fibers used to make the matrix is within the range of from about 1 to 1.5 $lbs/in^2$. Furthermore, it is desirable for the filter to possess relatively free access of blood through pores from an upstream side where blood is fed to a downstream side where filtered blood is released. The pores may be of any cross sectional design, however, for this application an oval shape is preferred.

The aforementioned design parameters are selected to minimize the risk of clogging. In this regard, it is also desirable for the matrix to have a gradient construct in which the upstream side possesses relatively large pores to separate out the larger white blood cells, and the downstream side possesses smaller pores to remove the smaller white blood cells. In this configuration, clogging is less likely because the larger cells will not reach the smaller pores in which they would most likely be trapped.

In a further desirable aspect of the invention, the pore size of the leukocyte removal matrix is within the range of from about 5 µm to 500 µm, preferably about 10 µm to about 250 µm, and more preferably about 50 µm to about 150 µm. In a desirable aspect of the invention, the leukocyte removal matrix has an upstream side for entry of a sample to be filtered and a downstream side for exit of a filtered sample. The matrix has a gradient of pore sizes from larger pore sizes from about 50 µm to about 250 µm at the upstream side to from about 10 µm to about 50 µm at the downstream side. Preferably, the fibers forming the matrix have a diameter of from about 5 µm to about 15 µm.

Although not necessary, it is also possible to use a prefilter to remove microaggregates. This is especially important when filtering blood that has been stored for a relatively long period of time before the white blood cell removal process is performed.

Desirably, the leukocyte separation filter is a sheet of from about 0.025 mm to about 25 mm thick. A solution of polyurethane polymer, for example Biomer™ (Ethicon, Inc., Somerville, N.J.), in solvent is fed into a spinneret applicator. The spinneret has a circular nozzle through which a fiber having an average diameter of from about 5 µm to about 15 µm is fed. A series of passes of the moveable table in a sine wave pattern, with one layer of one polymer followed by a subsequent layer of the same or another polymer in a sine wave pattern at a 90° angle to the previous sine wave pattern, results in formation of a non-woven sheet having a wall thickness of from about 0.025 mm to about 25 mm, preferably from about 0.005 in to about 0.2 in (0.13 mm to about 5 mm). The sheet is cut to size to form a leukocyte filter which fits into a separation unit. Optionally, a macrocyte and/or granulocyte pre-filter is made in the same fashion as described above, except having a greater pore size than the leukocyte filter. The prefilter desirably has a pore size of at least about 50 μm, typically no greater than 150 μm. The pre-filter may be inserted into the separation unit or may be included in its own separation filter upstream from the leukocyte filter.

The matrix so formed is capable of filtering at least one unit of PRC. Desirably, the removal efficiency is removal of at least about 90%, preferably 95%, more preferably 98% and most preferably 99% of leukocytes from the unit of PRC. Residual leukocytes will be less than about $10 \times 10^5$, preferably less than $5 \times 10^5$, more preferably less than $2 \times 10^5$, most preferably less than $5 \times 10^4$.

Figure 4:
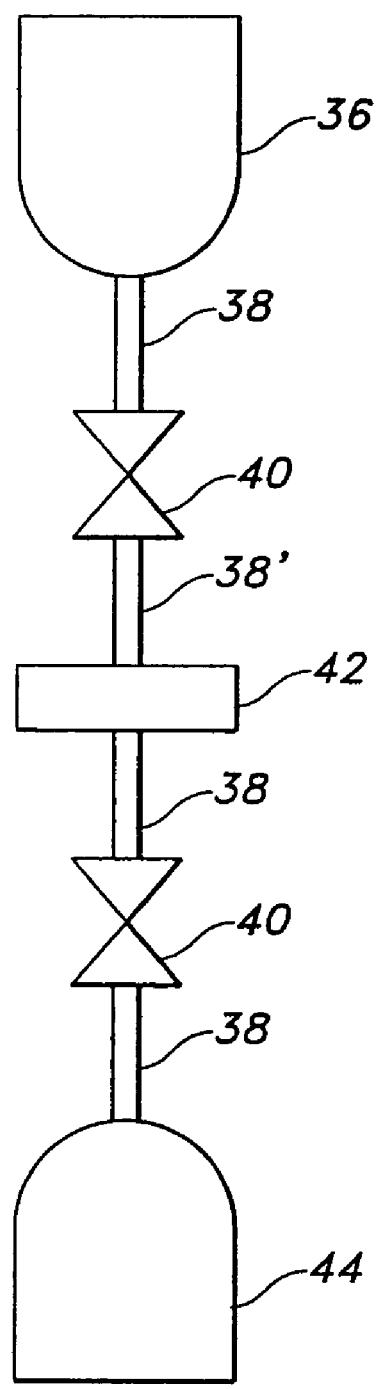
FIG. 4 is an embodiment of a blood separation device according to the present invention.

An assembly for using the matrix for separating leukocytes from blood is shown in FIG. 4. A blood bag 36 is in fluid communication with tubing 38. The rate of feed can be regulated by a valve 40. Tubing 38 conveys the unfiltered blood from the blood bag 36 to a filter casing 42 including the matrix therein (not shown). The filtered blood is then conveyed along tubing 28 through an additional valve 40 and further tubing 28 to a filtrate blood bag 44 for collection and subsequent storage or use. The rate of flow from the filter casing 32 to the filtrate blood bag 36 may be regulated with an additional valve 34. In this example, gravity is used to introduce the blood into the blood separation unit. However, it is also possible to use other methods to introduce blood into the matrix as is known in the art. These other methods of drawing blood through the separation unit are also within the contemplation of the inventors. When using the assembly for filtering blood, it may be used alone or the blood may first be treated with an anticoagulant.

It will be apparent that the present invention has been described herein with reference to certain preferred or exemplary embodiments. The preferred or exemplary embodiments described herein may be modified, changed, added to, or deviated from without departing from the intent, spirit and scope of the present invention, and it is intended that all such additions, modifications, amendments and/or deviations be included within the scope of the following claims.

We claim:

1. A non-woven matrix material for use in a medical device for removing leukocytes from blood suspensions comprising a non-woven three dimensional matrix of one or more polymeric fibers wherein said matrix has a predetermined shape, a predetermined pore volume fraction of substantially parallel pores including a defined channel configuration, a predetermined pore size, and a plurality of connections between said fibers,
    wherein the matrix material:
    (a) has a first upstream side and a second downstream side, the first side being arranged toward the inlet and the second side being arranged toward the outlet; and
    (b) has a gradient construct in which the upstream side possesses relatively large pores and the downstream side possesses smaller pores.

2. A non-woven matrix material for use in a medical device for removing leukocytes from blood suspensions comprising a non-woven three dimensional matrix of one or more polymeric fibers, wherein said matrix is formed by a method of selectively generating a uniform or varied micro-architecture within the three dimensional non-woven matrix, comprising the steps of:
    admixing at least one fiber forming polymer with a compatible solvent to form a flowable polymer mixture;
    applying at least one fiber formed from said polymer mixture to a moveable table capable of motion in a first plane (x), a second plane (y) perpendicular to said first plane, and a third plane (z) perpendicular to said first plane (x) and said second plane (y); and
    controlling movement of at least said table so as to form a three dimensional non-woven matrix of fibers having a predetermined pore volume fraction of substantially parallel pores, including a defined channel configuration, a predetermined pore size, and a plurality of connections between said fibers,
    wherein the matrix material:
    (a) has a first upstream side and a second downstream side, the first side being arranged toward the inlet and the second side being arranged toward the outlet; and
    (b) has a gradient construct in which the upstream side possesses relatively large pores and the downstream side possesses smaller pores.

3. The matrix material according to claim 1, wherein said predetermined pore volume fraction is from about 15% to about 98%.

4. The matrix material according to claim 1, wherein said polymeric fibers are formed from a biocompatible thermoplastic polymer.

5. The matrix material according to claim 1, wherein said polymer is selected from the group consisting of an alginate, a hyaluronic acid, a cellulose, a dextran, a pullane, a polyhyaluronic acid, a chitin, a poly(3-hydroxyalkanoate), a poly(3-hydroxyoctanoate), a poly(3-hydroxyfatty acid), a collagen, a zein, a casein, a gelatin, a gluten, a serum albumen, a polyphosphazene, poly(vinyl alcohol), a polyamide, a polyester amide, a poly(amino acid), a polyanhydride, a polyester, a polycarbonate, a polyacrylate, a polyalkylene, a polyacrylamide, a polyalkylene glycol, a polyalkylene oxide, a polyalkylene terephthalate, a polyortho ester, a polyvinyl ether, a polyvinyl ester, a polyvinyl halide, a polyvinyl pyrrolidone, a polylactide, a polyglyxolide, a polysiloxane, a polycaprolactone, a polyhydroxybutrate, a polyurethane, a poly α-hydroxy acid, a poly L-lactic acid, a polyglycolic acid, a styrene isobutylstyrene block polymer and blends and copolymers thereof.

6. The matrix material according to claim 1, wherein said matrix has a pore volume fraction of from about 15% to about 90%.

7. The matrix material according to claim 1, wherein said matrix has a pore size of from about 5 microns to about 500 microns.

8. The matrix material according to claim 1, wherein said matrix has a pore size of from about 50 microns to about 150 microns.

9. The matrix material according to claim 1, wherein said pores are arranged substantially continuously throughout a depth of said matrix.

10. The matrix material according to claim 1, wherein said pores are arranged substantially discontinuously throughout a depth of said matrix.

11. The matrix material according to claim 1, wherein said polymeric fibers possess an average diameter of from about 1 micron to about 40 microns.

12. The matrix material according to claim 1, wherein said polymeric fibers possess an average diameter of from about 5 microns to about 15 microns.

13. The matrix material according to claim 1, wherein said matrix is at least partially degradable having a predetermined rate of degradation.

14. A non-woven polymeric matrix for separating leukocytes from a blood sample, said matrix having a first upstream side and a second downstream side, and comprising:
- a non-woven three dimensional matrix formed from one or more polymeric fibers having a diameter of from about 5 µm to about 15 µm, the matrix having a predetermined pore volume fraction of substantially parallel pores, including a defined channel configuration, a predetermined pore size in the range of from about 10 µm to about 250 µm, a plurality of connections between said fibers, and being configured so as to remove at least about 98% of leukocytes from at least one unit of packed red blood cells,
- wherein the matrix material has a gradient construct in which the upstream side possesses relatively large pores and the downstream side possesses smaller pores.

15. The matrix according to claim 14, wherein said matrix further comprises a therapeutic agent.

16. The matrix according to claim 15, wherein said therapeutic agent is an anticoagulant.

17. The matrix according to claim 14, wherein said pores are arranged substantially parallel with a flow of blood therethrough.

18. The matrix according to claim 14, wherein each of said pores runs substantially continuously from the first upstream side of said matrix to the second downstream side of said matrix.

19. The matrix according to claim 14, wherein each of said pores runs substantially discontinuously from the first upstream side of said matrix to the second downstream side of said matrix.

20. A non-woven matrix material according to claim 1 wherein the tensile strength of the polymeric fibers used to make the matrix is within the range of from about 0.5 to 5.0 lbs/in$^2$.

21. A non-woven matrix material according to claim 1 wherein (a) the matrix has a removal efficiency of at least about 90% of leukocytes from a unit of PRC; and (b) residual leukocytes will be less than about $10 \times 10^5$.

22. A non-woven matrix material for use in a medical device for removing leukocytes from blood suspensions comprising a non-woven three dimensional matrix of one or more polymeric fibers wherein:
- (a) the matrix material:
  - (i) has a first upstream side and a second downstream side, the first side being arranged toward the inlet and the second side being arranged toward the outlet; and
  - (ii) has a gradient construct in which the upstream side possesses relatively large pores and the downstream side possesses smaller pores;
- (b) said matrix has a predetermined shape, a predetermined pore volume fraction of substantially parallel pores, in the range of 15% to about 98% including a defined channel configuration, a predetermined pore size, and a plurality of connections between said plurality of fibers; and
- (c) said polymer is selected from the group consisting of an alginate, a hyaluronic acid, a cellulose, a dextran, a pullane, a polyhyaluronic acid, a chitin, a poly(3-hydroxyalkanoate), a poly(3-hydroxyoctanoate), a poly(3-hydroxyfatty acid), a collagen, a zein, a casein, a gelatin, a gluten, a serum albumen, a polyphosphazene, poly(vinyl alcohol), a polyamide, a polyester amide, a poly(amino acid), a polyanhydride, a polyester, a polycarbonate, a polyacrylate, a polyalkylene, a polyacrylamide, a polyalkylene glycol, a polyalkylene oxide, a polyalkylene terephthalate, a polyortho ester, a polyvinyl ether, a polyvinyl ester, a polyvinyl halide, a polyvinyl pyrrolidone, a polylactide, a polyglyxolide, a polysiloxane, a polycaprolactone, a polyhydroxybutrate, a polyurethane, a poly α-hydroxy acid, a poly L-lactic acid, a polyglycolic acid, a styrene isobutylstyrene block polymer and blends and copolymers thereof.

* * * * *

UNITED STATES PATENT AND TRADEMARK OFFICE
CERTIFICATE OF CORRECTION

| | | |
|---|---|---|
| PATENT NO. | : 7,661,541 B2 | Page 1 of 1 |
| APPLICATION NO. | : 11/496187 | |
| DATED | : February 16, 2010 | |
| INVENTOR(S) | : Dao et al. | |

It is certified that error appears in the above-identified patent and that said Letters Patent is hereby corrected as shown below:

Col. 2, line 20, after "in", change "ibis" to --this--.

Col. 2, line 65, after "sizes", delete "and".

Col. 4, line 10, before "a liquid", change "Loin" to --form--.

Col. 4, line 51, after "methods", change "form" to --forms--.

Col. 6, line 45, after "regulated", change "byte" to --by the--.

Col. 6, line 62, after "co-glycolic", change "avid" to --acid--.

Col. 11, line 65, after "invention", change "fall" to --falls--.

Signed and Sealed this

Twentieth Day of April, 2010

David J. Kappos
*Director of the United States Patent and Trademark Office*